(12) United States Patent
Ito

(10) Patent No.: US 10,952,598 B2
(45) Date of Patent: Mar. 23, 2021

(54) ENDOSCOPE SYSTEM AND IMAGE ACQUISITION METHOD WITH RED SIGNAL GENERATOR

(71) Applicant: OLYMPUS CORPORATION, Hachioji (JP)

(72) Inventor: Koichiro Ito, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 439 days.

(21) Appl. No.: 15/983,091

(22) Filed: May 18, 2018

(65) Prior Publication Data

US 2018/0263479 A1 Sep. 20, 2018

Related U.S. Application Data

(63) Continuation of application No. PCT/JP2016/081681, filed on Oct. 26, 2016.

(30) Foreign Application Priority Data

Nov. 25, 2015 (JP) .............................. JP2015-229766

(51) Int. Cl.
*A61B 1/06* (2006.01)
*A61B 1/04* (2006.01)
(Continued)

(52) U.S. Cl.
CPC ........ *A61B 1/0638* (2013.01); *A61B 1/00009* (2013.01); *A61B 1/00186* (2013.01);
(Continued)

(58) Field of Classification Search
CPC ....... A61B 1/04; A61B 1/0638; A61B 1/0646; A61B 1/00186; A61B 1/00009;
(Continued)

(56) References Cited

U.S. PATENT DOCUMENTS

| 4,951,130 A | * | 8/1990 | Iizuka | ............... H01L 31/02162 |
| | | | | 348/274 |
| 2003/0165266 A1 | * | 9/2003 | Kagawa | ............... H04N 1/6058 |
| | | | | 382/166 |

(Continued)

FOREIGN PATENT DOCUMENTS

| EP | 2116176 A1 | 11/2009 |
| EP | 2441374 A1 | 4/2012 |

(Continued)

OTHER PUBLICATIONS

International Search Report (ISR) dated Jan. 17, 2017 issued in International Application No. PCT/JP2016/081681.

(Continued)

*Primary Examiner* — John P Leubecker
(74) *Attorney, Agent, or Firm* — Holtz, Holtz & Volek PC

(57) ABSTRACT

The resolution of narrow band imaging is improved, while color reproducibility is improved when performing white-light observation. Provided is an endoscope system including an image pickup device having three types of color filters, said types being blue, green, and magenta, and also including an image processor that generates an image by processing a signal acquired by the image pickup device. The image processor includes a ratio calculator that calculates the ratio between a blue signal and a magenta signal, and also includes a red-signal generator that generates a red signal based on the ratio calculated by the ratio calculator.

8 Claims, 8 Drawing Sheets

(51) Int. Cl.
*H04N 5/235* (2006.01)
*H04N 9/04* (2006.01)
*G02B 23/24* (2006.01)
*A61B 1/00* (2006.01)
*H04N 9/07* (2006.01)
*H04N 5/225* (2006.01)
*H04N 9/73* (2006.01)

(52) U.S. Cl.
CPC .............. *A61B 1/04* (2013.01); *A61B 1/0646* (2013.01); *G02B 23/2484* (2013.01); *H04N 5/2256* (2013.01); *H04N 5/2354* (2013.01); *H04N 9/045* (2013.01); *H04N 9/04521* (2018.08); *H04N 9/07* (2013.01); *H04N 9/735* (2013.01); *G02B 23/2469* (2013.01); *H04N 2005/2255* (2013.01)

(58) Field of Classification Search
CPC .............. H04N 5/2256; H04N 5/2354; H04N 2005/2255; H04N 9/04557
See application file for complete search history.

(56) References Cited

U.S. PATENT DOCUMENTS

| | | | | |
|---|---|---|---|---|
| 2005/0264587 | A1* | 12/2005 | Kurumisawa | G09G 3/2003 345/690 |
| 2007/0135715 | A1* | 6/2007 | Inoue | G06T 7/90 600/477 |
| 2010/0032546 | A1 | 2/2010 | Kawano et al. | |
| 2011/0273548 | A1 | 11/2011 | Uchiyama et al. | |
| 2012/0075511 | A1 | 3/2012 | Tay | |
| 2015/0035107 | A1 | 2/2015 | Tay | |
| 2016/0270642 | A1 | 9/2016 | Morita | |
| 2016/0270643 | A1 | 9/2016 | Sasaki | |

FOREIGN PATENT DOCUMENTS

| | | |
|---|---|---|
| EP | 3085300 A1 | 10/2016 |
| EP | 3085301 A1 | 10/2016 |
| JP | H08009395 A | 1/1996 |
| JP | 2006211610 A | 8/2006 |
| JP | 2012170639 A | 9/2012 |
| JP | 2013539294 A | 10/2013 |
| JP | 2015053578 A | 3/2015 |
| JP | 2015116328 A | 6/2015 |
| WO | 2008105370 A1 | 9/2008 |
| WO | 2010143692 A1 | 12/2010 |
| WO | 2012038939 A2 | 3/2012 |
| WO | 2015093295 A1 | 6/2015 |

OTHER PUBLICATIONS

Written Opinion dated Jan. 17, 2017 issued in International Application No. PCT/JP2016/081681.

* cited by examiner

ENDOSCOPE SYSTEM AND IMAGE ACQUISITION METHOD WITH RED SIGNAL GENERATOR

CROSS-REFERENCE TO RELATED APPLICATIONS

This is a continuation of International Application PCT/JP2016/081681, with an international filing date of Oct. 26, 2016, which is hereby incorporated by reference herein in its entirety. This application claims the benefit of Japanese Patent Application No. 2015-229766, filed on Nov. 25, 2015, the content of which is incorporated herein by reference.

TECHNICAL FIELD

The present invention relates to endoscope systems and image acquisition methods.

BACKGROUND ART

A known endoscope system in the related art includes primary color filters for red (R), green (G), and blue (B) colors. A color filter having a main sensitivity region and a sub sensitivity region is disposed at each G pixel, and a component of the sub sensitivity region is extracted from a pixel value of the G pixel (e.g., see Patent Literature 1).

CITATION LIST

Patent Literature

{PTL 1}
Japanese Unexamined Patent Application, Publication No. 2012-170639

SUMMARY OF INVENTION

Technical Problem

The present invention provides an endoscope system and an image acquisition method that can improve the resolution of narrow band imaging and that can also improve color reproducibility when performing white-light observation.

Solution to Problem

An aspect of the present invention provides an endoscope system including an image pickup device having three types of B, G, and Mg color filters and an image processor that generates an image by processing a signal acquired by the image pickup device. The image processor includes a ratio calculator that calculates a ratio between a B signal and an Mg signal, and also includes an R-signal generator that generates an R signal based on the ratio calculated by the ratio calculator.

In the above aspect, the B signal and the Mg signal used for calculating the ratio in the ratio calculator are preferably signals acquired when an image is acquired under an image acquisition condition in which light having high intensity in a B region in the spectral characteristic and having relatively low intensity in an R region in the spectral characteristic enters the image pickup device.

In the above aspect, the R-signal generator may generate the R signal based on the following expression.

$$\begin{pmatrix} R \\ G \\ B \end{pmatrix} = \begin{pmatrix} 1 & 0 & -bMg/bB \\ 0 & 1 & 0 \\ 0 & 0 & 1 \end{pmatrix} \begin{pmatrix} Mg \\ G \\ B \end{pmatrix} \quad \{\text{Expression 1}\}$$

In this case, bB denotes the B signal when the image is acquired under the image acquisition condition in which the light having high intensity in the B region in the spectral characteristic enters the image pickup device, and bMg denotes the Mg signal when the image is acquired under the image acquisition condition in which the light having high intensity in the B region in the spectral characteristic enters the image pickup device.

In the above aspect, the B signal when generating the R signal may be a signal of a B pixel in close proximity to an Mg pixel.

Another aspect of the present invention provides an image acquisition method including a first step for performing image acquisition under a first image acquisition condition in which light having high intensity in a B region in the spectral characteristic and having relatively low intensity in an R region in the spectral characteristic enters an image pickup device, and a second step for performing image acquisition substantially simultaneously with the first step under a second image acquisition condition in which light having uniform intensity in R, G, and B regions in the spectral characteristic enters the image pickup device.

Another aspect of the present invention provides an endoscope system including an image pickup device having three types of B, G, and Mg color filters and an image processor that generates an image by processing a signal acquired by the image pickup device. The image processor includes a ratio calculator that calculates a ratio between a B signal and an Mg signal and a ratio between a G signal and the Mg signal, and also includes an R-signal generator that generates an R signal based on the ratios calculated by the ratio calculator.

According to this aspect, the Mg signal acquired by the image pickup device may sometimes have a G signal mixed therein in addition to an R signal and a B signal. The ratio calculator calculates the ratio between the B signal and the Mg signal and the ratio between the G signal and the Mg signal, and the R-signal generator generates the R signal based on these ratios, so that, by using the B signal and the R signal and G signal having no B signal mixed therein, a white-light image with high color reproducibility can be generated without color mixture.

In the above aspect, the B signal and the Mg signal used by the ratio calculator for calculating the ratio may be signals acquired when an image is acquired under an image acquisition condition in which light having high intensity in a B region in the spectral characteristic and having relatively low intensity in a G region and an R region in the spectral characteristic enters the image pickup device, and the G signal and the Mg signal used by the ratio calculator for calculating the ratio may be signals acquired when an image is acquired under an image acquisition condition in which light having high intensity in the G region in the spectral characteristic and having relatively low intensity in the B region and the R region in the spectral characteristic enters the image pickup device.

In the above aspect, the R-signal generator may generate the R signal based on the following expression.

$$\begin{pmatrix} R \\ G \\ B \end{pmatrix} = \begin{pmatrix} 1 & -gMg/gG & -bMg/bB \\ 0 & 1 & 0 \\ 0 & 0 & 1 \end{pmatrix} \begin{pmatrix} Mg \\ G \\ B \end{pmatrix} \quad \{\text{Expression 2}\}$$

In this case, bB denotes the B signal when the image is acquired under the image acquisition condition in which the light having high intensity in the B region in the spectral characteristic enters the image pickup device, bMg denotes the Mg signal when the image is acquired under the image acquisition condition in which the light having high intensity in the B region in the spectral characteristic enters the image pickup device, gG denotes the G signal when the image is acquired under the image acquisition condition in which the light having high intensity in the G region in the spectral characteristic enters the image pickup device, and gMg denotes the Mg signal when the image is acquired under the image acquisition condition in which the light having high intensity in the G region in the spectral characteristic enters the image pickup device.

In the above aspect, the B signal and the G signal used when generating the R signal may be signals of a B pixel and a G pixel in close proximity to an Mg pixel.

Another aspect of the present invention provides an image acquisition method including a first step for performing image acquisition under a first image acquisition condition in which light having high intensity in a B region in the spectral characteristic and having relatively low intensity in a G region and an R region in the spectral characteristic enters an image pickup device, and a second step for performing image acquisition under a second image acquisition condition in which light having high intensity in the G region in the spectral characteristic and having relatively low intensity in the B region and the R region in the spectral characteristic enters the image pickup device.

In the above aspect, the image acquisition method may further include a third step for performing image acquisition under a third image acquisition condition in which light having uniform intensity in the R, G, and B regions in the spectral characteristic enters the image pickup device.

Another aspect of the present invention provides an endoscope system including an image pickup device having three types of B, Cy, and R color filters and an image processor that generates an image by processing a signal acquired by the image pickup device. The image processor includes a ratio calculator that calculates a ratio between a B signal and a Cy signal, and also includes a G-signal generator that generates a G signal based on the ratio calculated by the ratio calculator.

In the above aspect, the B signal and the Cy signal used for calculating the ratio in the ratio calculator are preferably signals acquired when an image is acquired under an image acquisition condition in which light having high intensity in a B region in the spectral characteristic and having relatively low intensity in a G region in the spectral characteristics enters the image pickup device.

In the above aspect, the G-signal generator may generate the G signal based on the following expression.

$$\begin{pmatrix} R \\ G \\ B \end{pmatrix} = \begin{pmatrix} 1 & 0 & 0 \\ 0 & 1 & -bCy/bB \\ 0 & 0 & 1 \end{pmatrix} \begin{pmatrix} R \\ Cy \\ B \end{pmatrix} \quad \{\text{Expression 3}\}$$

In this case, bB denotes the B signal when the image is acquired under the image acquisition condition in which the light having high intensity in the B region in the spectral characteristic enters the image pickup device, and bCy denotes the Cy signal when the image is acquired under the image acquisition condition in which the light having high intensity in the B region in the spectral characteristic enters the image pickup device.

In the above aspect, the B signal when generating the G signal may be a signal of a B pixel in close proximity to a Cy pixel.

Another aspect of the present invention provides an image acquisition method including a first step for performing image acquisition under a first image acquisition condition in which light having high intensity in a B region in the spectral characteristic and having relatively low intensity in a G region in the spectral characteristic enters an image pickup device, and a second step for performing image acquisition substantially simultaneously with the first step under a second image acquisition condition in which light having uniform intensity in R, G, and B regions in the spectral characteristic enters the image pickup device.

Another aspect of the present invention provides an endoscope system including an image pickup device having three types of B, Cy, and Mg color filters and an image processor that generates an image by processing a signal acquired by the image pickup device. The image processor includes a ratio calculator that calculates a ratio between a B signal and an Mg signal and a ratio between the B signal and a Cy signal, and also includes an RG-signal generator that generates an R signal and a G signal based on the ratios calculated by the ratio calculator.

In the above aspect, the B signal, the Mg signal, and the Cy signal used for calculating the ratios in the ratio calculator are preferably signals acquired when an image is acquired under an image acquisition condition in which light having high intensity in a B region in the spectral characteristic and having relatively low intensity in a G region and an R region in the spectral characteristic enters the image pickup device imaging element.

In the above aspect, the RG-signal generator may generate the R signal and the G signal based on the following expression.

$$\begin{pmatrix} R \\ G \\ B \end{pmatrix} = \begin{pmatrix} 1 & 0 & -bMg/bB \\ 0 & 1 & -bCy/bB \\ 0 & 0 & 1 \end{pmatrix} \begin{pmatrix} Mg \\ Cy \\ B \end{pmatrix} \quad \{\text{Expression 4}\}$$

In this case, bB denotes the B signal when the image is acquired under the image acquisition condition in which the light having high intensity in the B region in the spectral characteristic enters the image pickup device, bMg denotes the Mg signal when the image is acquired under the image acquisition condition in which the light having high intensity in the B region in the B region spectral characteristic enters the image pickup device, and bCy denotes the Cy signal when the image is acquired under the image acquisition condition in which the light having high intensity in the B region in the spectral characteristic enters the image pickup device imaging element.

In the above aspect, the B signal when generating the R signal may be a signal of a B pixel in close proximity to an Mg pixel, and the B signal when generating the G signal may be a signal of a B pixel in close proximity to a Cy pixel.

Another aspect of the present invention provides an image acquisition method including a first step for performing image acquisition under a first image acquisition condition in which light having high intensity in a B region in the spectral characteristic and having relatively low intensity in a G region and an R region in the spectral characteristic enters an image pickup device, and a second step for performing image acquisition substantially simultaneously with the first step under a second image acquisition condition in which light having uniform intensity in R, G, and B regions in the spectral characteristic enters the image pickup device.

Another aspect of the present invention provides an endoscope system including an image pickup device having three types of B, Cy, and Mg color filters and an image processor that generates an image by processing a signal acquired by the image pickup device. The image processor includes a ratio calculator that calculates a ratio between a B signal and an Mg signal, a ratio between the B signal and a Cy signal, and a ratio between the Cy signal and the Mg signal, and also includes an RG-signal generator that generates an R signal and a G signal based on the ratios calculated by the ratio calculator.

In the above aspect, the B signal and the Mg signal used by the ratio calculator for calculating the ratio between the B signal and the Mg signal and the ratio between the B signal and the Cy signal may be signals acquired when an image is acquired under an image acquisition condition in which light having high intensity in a B region in the spectral characteristic and having relatively low intensity in a G region and an R region in the spectral characteristic enters the image pickup device, and the Cy signal and the Mg signal used by the ratio calculator for calculating the ratio between the Cy signal and the Mg signal may be signals acquired when an image is acquired under an image acquisition condition in which light having high intensity in the G region in the spectral characteristic and having relatively low intensity in the B region and the R region in the spectral characteristic enters the image pickup device.

In the above aspect, the RG-signal generator may generate the R signal and the G signal based on the following expression.

$$\begin{pmatrix} R \\ G \\ B \end{pmatrix} = \begin{pmatrix} 1 & -gMg/gCy & -bMg/bB \\ 0 & 1 & -bCy/bB \\ 0 & 0 & 1 \end{pmatrix} \begin{pmatrix} Mg \\ Cy \\ B \end{pmatrix}$$ {Expression 5}

In this case, bB denotes the B signal when the image is acquired under the image acquisition condition in which the light having high intensity in the B region in the spectral characteristic enters the image pickup device, bMg denotes the Mg signal when the image is acquired under the image acquisition condition in which the light having high intensity in the B region in the spectral characteristic enters the image pickup device, bCy denotes the Cy signal when the image is acquired under the image acquisition condition in which the light having high intensity in the B region in the spectral characteristic enters the image pickup device, gMg denotes the Mg signal when the image is acquired under the image acquisition condition in which the light having high intensity in the G region in the spectral characteristic enters the image pickup device, and gCy denotes the Cy signal when the image is acquired under the image acquisition condition in which the light having high intensity in the G region in the spectral characteristic enters the image pickup device.

In the above aspect, the B signal and the Cy signal used when generating the R signal may be signals of a B pixel and a Cy pixel in close proximity to an Mg pixel, and the B signal used when generating the G signal may be a signal of a B pixel in close proximity to a Cy pixel.

DESCRIPTION OF EMBODIMENTS

An endoscope system 1 and an image acquisition method according to a first embodiment of the present invention will be described below with reference to the drawings.

Figure 1:
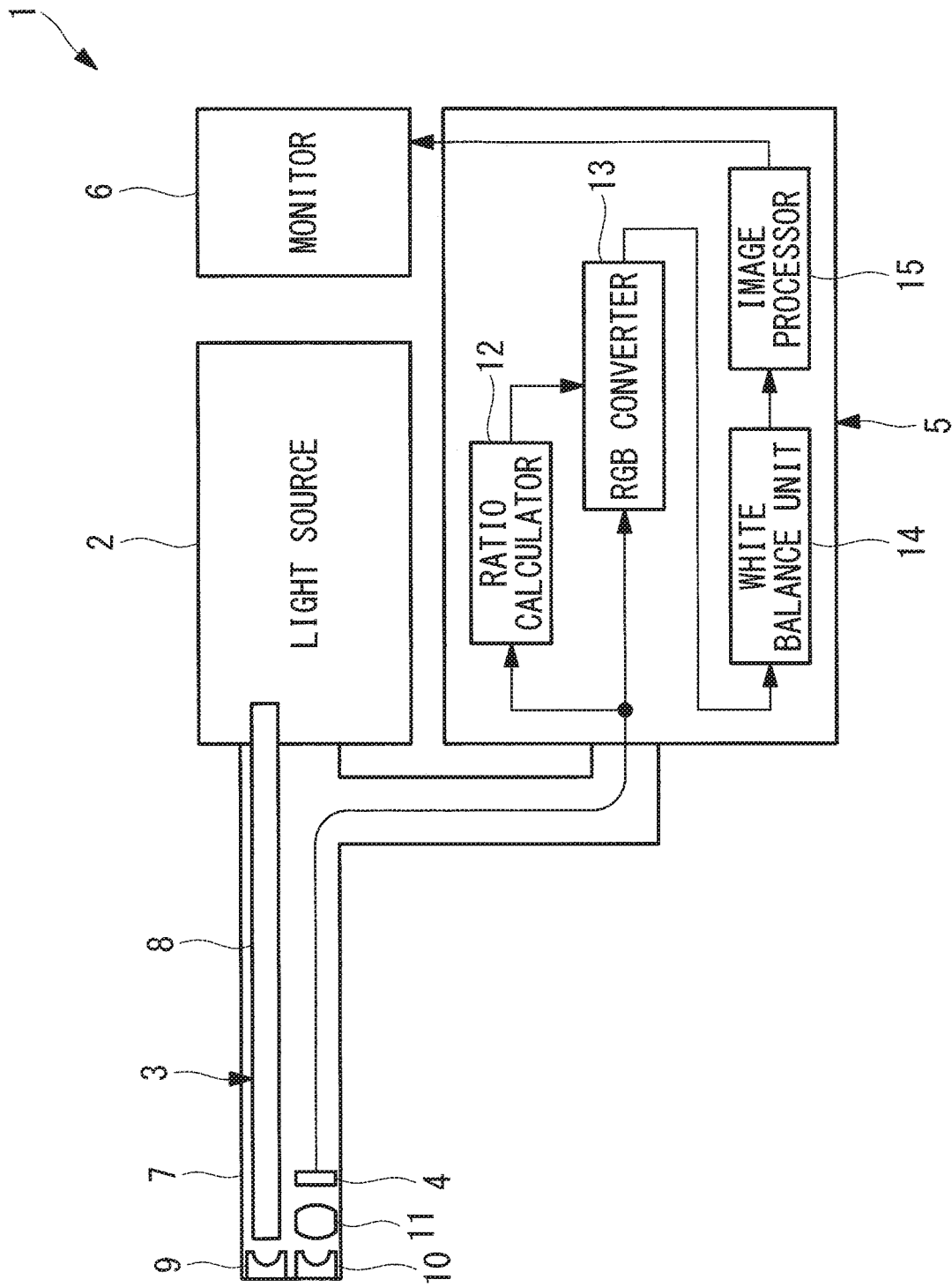
FIG. 1 illustrates the overall configuration of an endoscope system according to a first embodiment of the present invention.

As shown in FIG. 1, the endoscope system 1 according to this embodiment includes a light source 2 that outputs white light and narrow-band light, an endoscope 3 to be inserted into the body of a patient, an image pickup device 4 provided in the endoscope 3, an image processor 5 that processes a signal acquired by the image pickup device 4, and a monitor 6 that displays an image generated by the image processor 5.

The image acquisition method according to this embodiment includes a first step for performing image acquisition under a first image acquisition condition in which light having high intensity in a first region in the spectral characteristics and having relatively low intensity in a second region in the spectral characteristics (i.e., higher than 0 and lower than in the first region in the spectral characteristics) enters the image pickup device 4, and a second step for performing image acquisition substantially simultaneously with the first step under a second image acquisition condition in which light having uniform intensity in all regions in the spectral characteristics enters the image pickup device 4.

The endoscope 3 includes a light guide fiber 8 that is disposed in the longitudinal direction of a narrow insertion section 7 and that optically guides the light from the light source 2, an illuminating lens 9 that radiates the light optically guided by the light guide fiber 8 to an observation site within the body, an objective lens 10 and a focusing lens 11 that focus feedback light from within the body, and the image pickup device 4 that acquires an image of the feedback light focused by the focusing lens 11.

Figure 2:
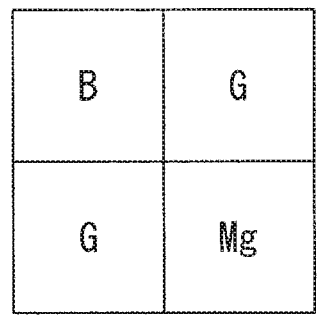
FIG. 2 illustrates the arrangement of color filters provided in an image pickup device of the endoscope system in FIG. 1.
Figure 3:
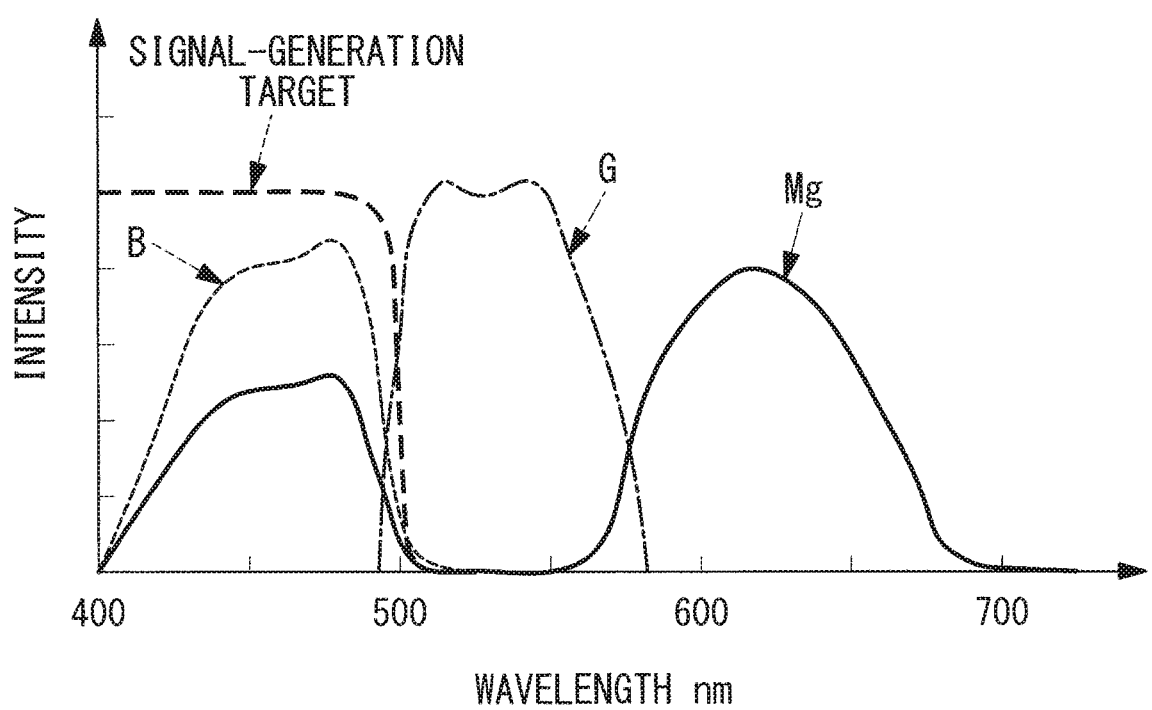
FIG. 3 illustrates the spectral characteristics of the color filters in FIG. 2.

The image pickup device 4 includes color filters shown in FIGS. 2 and 3 for each pixel. In the example shown in FIG. 2, the color filters have a periodically-repeating pattern in which a red (R) color filter in primary color filters arranged in a so-called Bayer pattern is replaced with a magenta (Mg) color filter.

The Mg color filter has the spectral characteristic shown in FIG. 3. Specifically, the spectral characteristic has a high intensity in the blue (B) region and the red (R) region and has relatively low intensity (close to zero) in the green (G) region.

Specifically, due to the relatively small number of B pixels in a general Bayer pattern having primary color filters, the resolution in narrow band imaging (NBI) in which observation is performed by radiating narrow-band light in the B region onto an observation site is low. By replacing the R color filter with an Mg color filter having sensitivity to the B region, the resolution of an image in narrow band imaging can be improved.

As shown in FIG. 1, the image processor 5 includes a ratio calculator 12 that calculates the ratio between a B signal and an Mg signal from a B signal and an Mg signal acquired by the image pickup device 4, an RGB converter (R-signal generator) 13 that generates an R signal based on the ratio calculated by the ratio calculator 12, a white balance unit 14 that adjusts the white balance of the R signal generated by the RGB converter 13 and the B signal and a G signal acquired by the image pickup device 4, and an image processor 15 that generates a white-light image by using the white-balance-adjusted R signal, G signal, and B signal.

Figure 4:
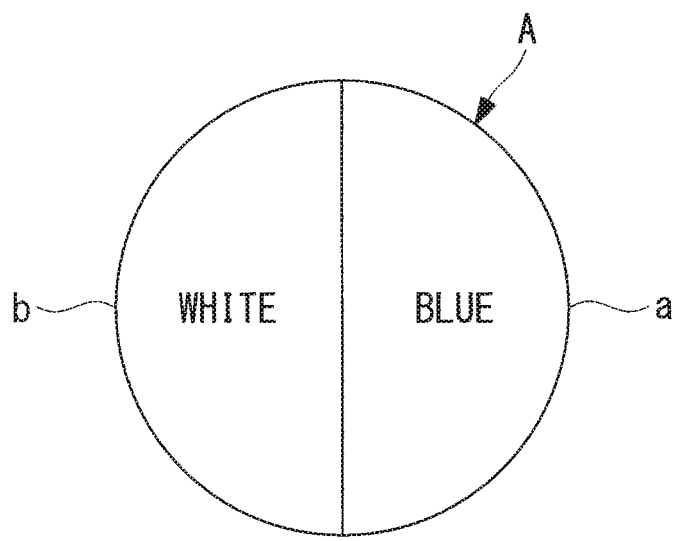
FIG. 4 illustrates an example of a signal-generation target used in the endoscope system in FIG. 1.

The B signal and the Mg signal to be used when the ratio calculator 12 calculates the ratio are preferably signals acquired by acquiring an image of a signal-generation target. A shown in FIG. 4. As shown in FIG. 3, the signal-generation target A is, for example, a blue target having a spectral characteristic having high intensity in the B region and relatively low intensity in the R region. In the example shown in FIG. 4, the signal-generation target A is a disk-shaped plate having a blue first region a and a white second region b.

The RGB converter 13 generates an R signal by using the ratio calculated by the ratio calculator 12. Specifically, the RGB converter 13 uses mathematical expression 6 to calculate a B signal, a G signal, and an R signal from the B signal, G signal, and Mg signal acquired by the image pickup device 4.

$$\begin{pmatrix} R \\ G \\ B \end{pmatrix} = \begin{pmatrix} 1 & 0 & -bMg/bB \\ 0 & 1 & 0 \\ 0 & 0 & 1 \end{pmatrix} \begin{pmatrix} Mg \\ G \\ B \end{pmatrix} \quad \{\text{Expression 6}\}$$

In this case, bB denotes a B signal when an image of the signal-generation target A is acquired, and bMg denotes an Mg signal when the image of the signal-generation target A is acquired.

According to mathematical expression 6, the B signal and the G signal output from the RGB converter 13 are the B signal and the G signal acquired by the image pickup device 4, whereas the R signal alone is generated by subtracting from the Mg signal a signal obtained by multiplying the B signal by the ratio calculated by the ratio calculator 12.

In the endoscope system 1 according to this embodiment having the above-described configuration, an Mg color filter is provided in place of the R color filter in primary color filters used in a general Bayer pattern, so that high resolution observation can be performed in narrow band imaging. In addition, since an R signal not including a B signal is generated by using the ratio between a B signal and an Mg signal from an acquired Mg signal having a mixture of the B region and the R region, white-light observation with high color reproducibility can advantageously be performed.

In the image acquisition method according to this embodiment, the signal-generation target A has the first region a having a spectral characteristic with high intensity in the B region and relatively low intensity in the R region, so that, when a B signal and an Mg signal are acquired for calculating the ratio, an image of the first region a is acquired under the first image acquisition condition by the endoscope 3 (first step), whereby the accuracy of the calculated ratio can be readily improved.

When acquiring the image of the first region a under the first image acquisition condition, an image of the second region b is also simultaneously acquired under the second image acquisition condition (second step), so that a coefficient required for the white balance can be readily calculated. This is advantageous in terms of saving time and effort.

In this embodiment, when the RGB converter 13 calculates an R signal, it is preferable that a B signal in close proximity to an Mg pixel be used. If there is a change of color in the observation site, a smooth color change can be reproduced by using information obtained by acquiring an image of a position in close proximity.

In this embodiment, the spectral characteristic of the signal-generation target A has high intensity only in the B region. Alternatively, if the intensity of the G region is low in the spectral characteristic of the Mg color filter, the signal-generation target A used may have a high intensity also in the G region. The ratio can be similarly calculated with high accuracy without the signal in the G region mixing with the Mg signal.

Figure 5:
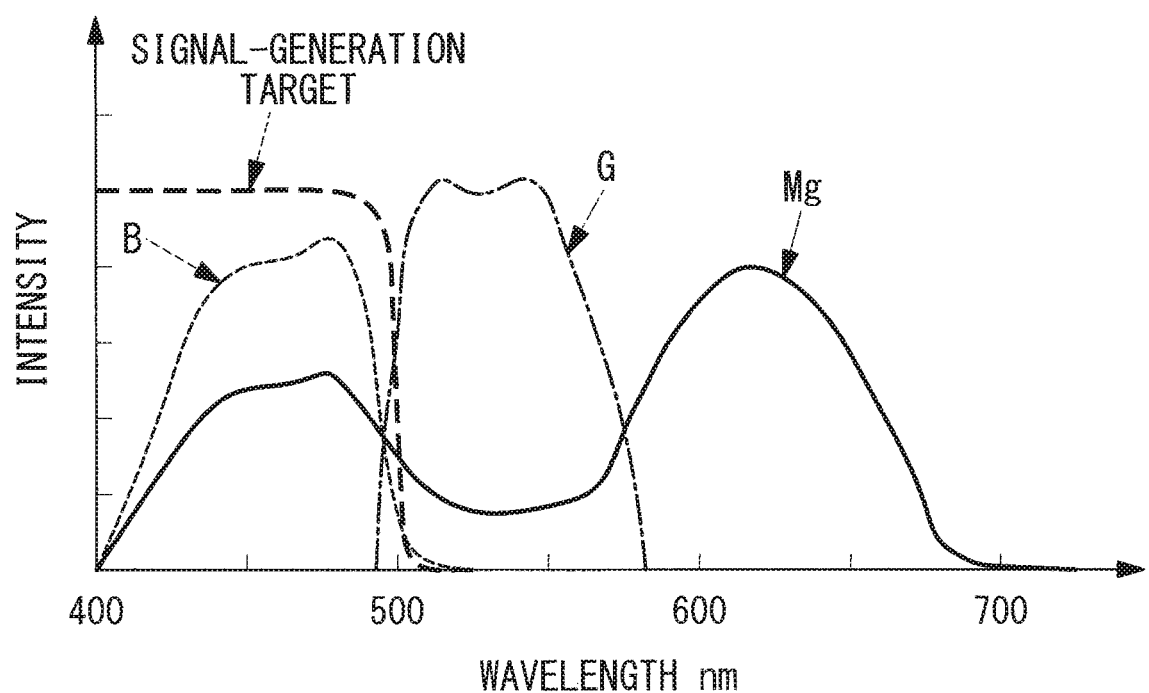
FIG. 5 illustrates a modification of the spectral characteristics of the color filters in FIG. 3.

As shown in FIG. 5, if the spectral characteristic of the Mg color filter has high intensity in the G region, it is preferable that the following configuration be employed.

Specifically, the ratio calculator 12 may calculate the ratio between the B signal and the Mg signal and the ratio between the G signal and the Mg signal, and the RGB converter 13 may generate an R signal based on the two ratios.

In this case, the B signal and the Mg signal to be used for calculating the ratio are signals acquired when an image of a blue target having high intensity in the B region in the spectral characteristic and having relatively low intensity in the G region and the R region in the spectral characteristic is acquired, and the G signal and the Mg signal are signals acquired when an image of a green target having high intensity in the G region in the spectral characteristic and having relatively low intensity in the B region and the R region in the spectral characteristic is acquired.

Figure 6:
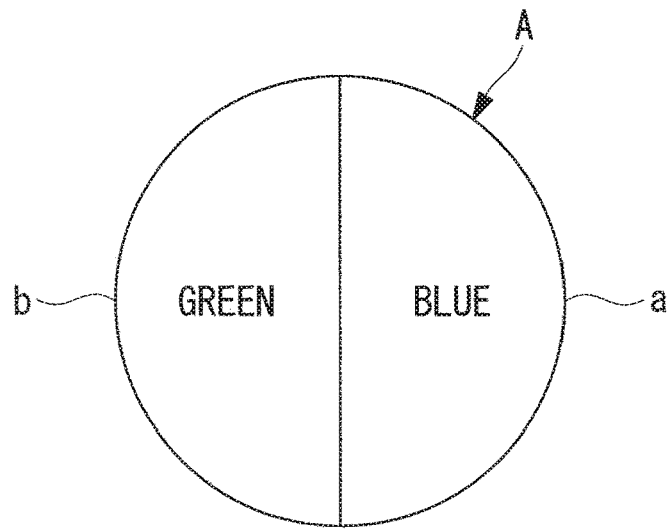
FIG. 6 illustrates a modification of the signal-generation target used in the endoscope system to which the color filters having the spectral characteristics in FIG. 3 are attached.
Figure 7:
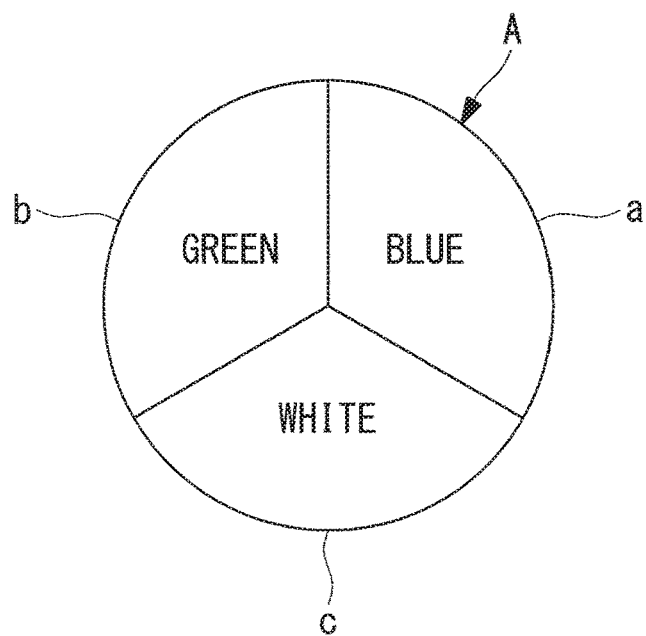
FIG. 7 illustrates another modification of the signal-generation target used in the endoscope system to which the color filters having the spectral characteristics in FIG. 3 are attached.

Therefore, the signal-generation target A used may have a blue first region a and a green second region b, as shown in FIG. 6, or may further have a white third region c, as shown in FIG. 7. In this case, the image acquisition method may include acquiring images of the first region a and the second region b, and subsequently acquiring an image of the third region c under a third image acquisition condition in which light having uniform intensity in the R region, the G region, and the B region in the spectral characteristic enters the image pickup device 4 (third step).

The calculation in the RGB converter 13 in this case may be performed in accordance with mathematical expression 7.

$$\begin{pmatrix} R \\ G \\ B \end{pmatrix} = \begin{pmatrix} 1 & -gMg/gG & -bMg/bB \\ 0 & 1 & 0 \\ 0 & 0 & 1 \end{pmatrix} \begin{pmatrix} Mg \\ G \\ B \end{pmatrix} \quad \{\text{Expression 7}\}$$

In this case, bB denotes a B signal when an image of the first region (blue) a of the signal-generation target A is acquired, bMg denotes an Mg signal when an image of the first region (blue) a of the signal-generation target A is acquired, gG denotes a G signal when an image of the second region (green) b of the signal-generation target A is acquired, and gMg denotes an Mg signal when an image of the second region (green) b of the signal-generation target A is acquired.

Accordingly, a signal in the B region corresponding to the ratio between the B signal and the Mg signal when the image of the first region a of the signal-generation target A is acquired can be subtracted from the Mg signal, and a signal in the G region corresponding to the ratio between the G signal and the Mg signal when the image of the second region b is acquired can be subtracted from the Mg signal. This is advantageous in that a part where B and G are mixed can be removed, so that a white-light image with high color reproducibility can be generated.

Next, an endoscope system and an image acquisition method according to a second embodiment of the present invention will be described below with reference to the drawings.

In the description of this embodiment, components identical to those in the endoscope system 1 according to the first embodiment described above are given the same reference signs, and descriptions thereof will be omitted.

The endoscope system according to this embodiment differs from the endoscope system 1 according to the first embodiment in terms of the color filters provided in the image pickup device 4 and the calculations in the ratio calculator 12 and the RGB converter 13.

Figure 8:
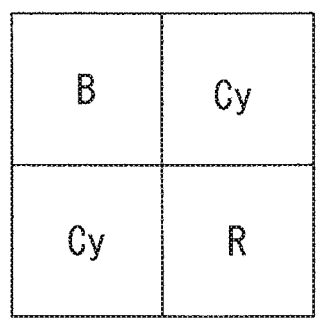
FIG. 8 illustrates the arrangement of color filters provided in an image pickup device of an endoscope system according to a second embodiment of the present invention.

As shown in FIG. 8, the color filters include cyan (Cy) color filters in place of G color filters in general primary color filters.

Figure 9:
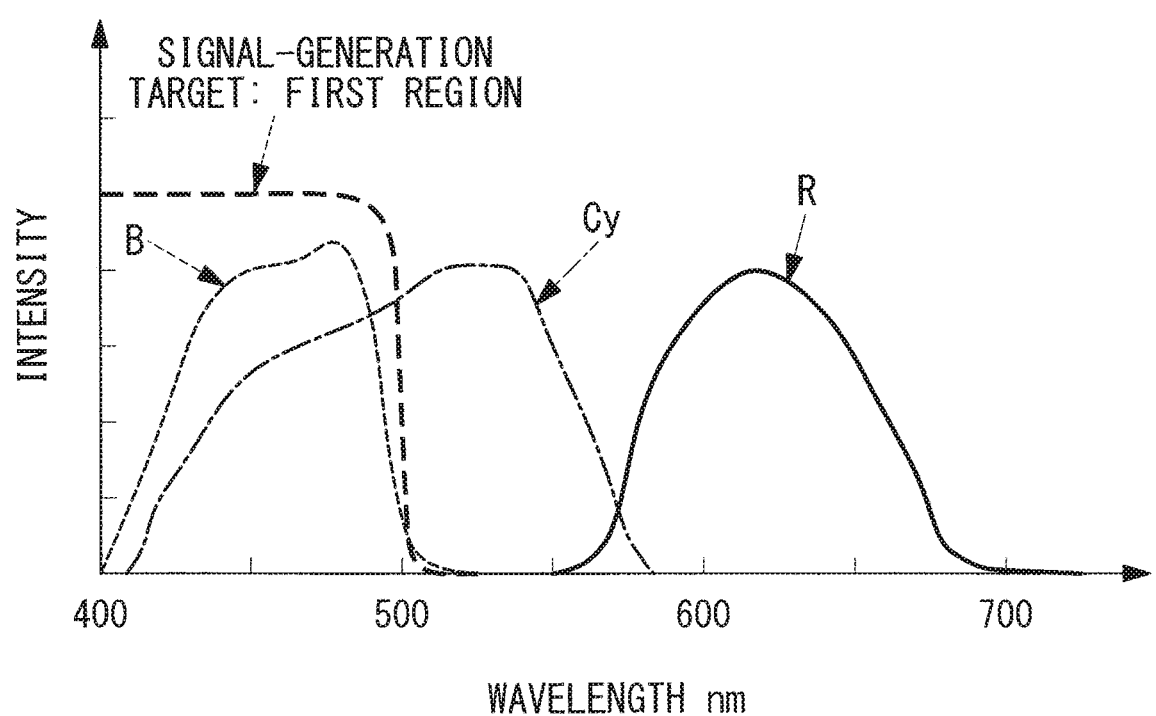
FIG. 9 illustrates the spectral characteristics of the color filters in FIG. 8.

As shown in FIG. 9, the Cy color filters have spectral characteristics having high intensity in the B region and the G region and having no intensity in the R region.

With a signal in the B region being included in a Cy signal, the resolution in narrow band imaging can be advantageously improved.

The ratio calculator 12 calculates the ratio between a B signal and a Cy signal. The signal-generation target A to be imaged when calculating the ratio is similar to that in the first embodiment.

The RGB converter (G-signal generator) 13 generates a G signal in accordance with mathematical expression 8.

$$\begin{pmatrix} R \\ G \\ B \end{pmatrix} = \begin{pmatrix} 1 & 0 & 0 \\ 0 & 1 & -bCy/bB \\ 0 & 0 & 1 \end{pmatrix} \begin{pmatrix} R \\ Cy \\ B \end{pmatrix} \quad \{\text{Expression 8}\}$$

In this case, bCy denotes a Cy signal when an image of the first region a of the signal-generation target A is acquired.

Accordingly, a signal in the B region corresponding to the ratio between the B signal and the Cy signal when the image of the first region (blue) a of the signal-generation target A is acquired can be subtracted from the Cy signal, so that a part where B is mixed can be removed, whereby a white-light image with high color reproducibility can be generated.

In this case, when the RGB converter 13 calculates a G signal, it is preferable that a B signal in close proximity to a Cy pixel be used. If there is a change of color in the observation site, a smooth color change can be reproduced by using information obtained by acquiring an image of a position in close proximity.

Next, an endoscope system and an image acquisition method according to a third embodiment of the present invention will be described below with reference to the drawings.

In the description of this embodiment, components identical to those in the endoscope system 1 according to the first embodiment described above are given the same reference signs, and descriptions thereof will be omitted.

The endoscope system according to this embodiment differs from the endoscope system 1 according to the first embodiment in terms of the color filters provided in the image pickup device 4 and the calculations in the ratio calculator 12 and the RGB converter 13.

Figure 10:
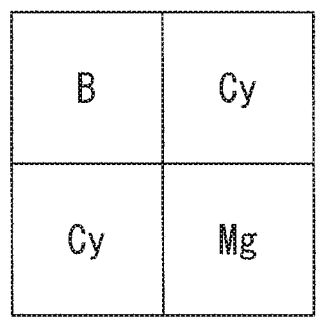
FIG. 10 illustrates the arrangement of color filters provided in an image pickup device of an endoscope system according to a third embodiment of the present invention.
Figure 11:
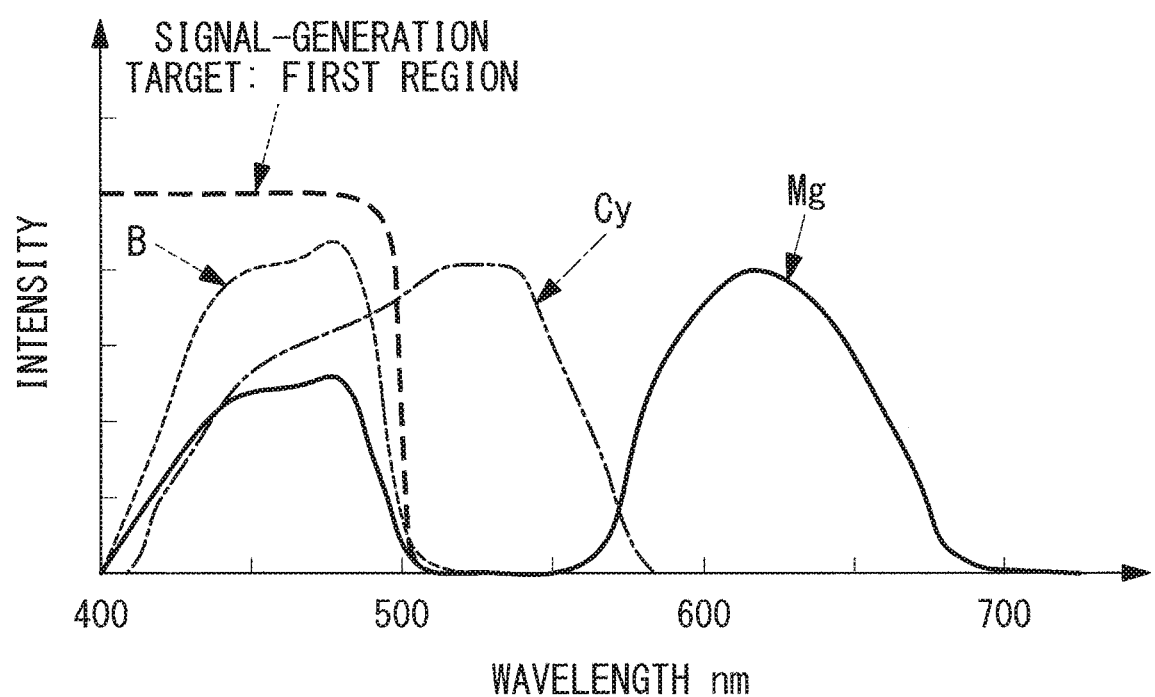
FIG. 11 illustrates the spectral characteristics of the color filters in FIG. 10.

As shown in FIG. 10, the color filters include Cy color filters in place of the G color filters in general primary color filters, and also include an Mg color filter in place of an R color filter. The spectral characteristics are shown in FIG. 11.

With a signal in the B region being included in both a Cy signal and an Mg signal, the resolution in narrow band imaging can be significantly improved.

The ratio calculator 12 calculates the ratio between a B signal and a Cy signal. The signal-generation target A to be imaged when calculating the ratio is similar to that in the first embodiment.

The RGB converter (RG-signal generator) 13 generates an R signal and a G signal in accordance with mathematical expression 9.

$$\begin{pmatrix} R \\ G \\ B \end{pmatrix} = \begin{pmatrix} 1 & 0 & -bMg/bB \\ 0 & 1 & -bCy/bB \\ 0 & 0 & 1 \end{pmatrix} \begin{pmatrix} Mg \\ Cy \\ B \end{pmatrix} \quad \{\text{Expression 9}\}$$

Accordingly, a signal in the B region corresponding to the ratio between the B signal and the Mg signal when the image of the signal-generation target A in the first region (blue) a is acquired can be subtracted from the Mg signal, so that a part where B is mixed can be removed. A signal in the B region corresponding to the ratio between the B signal and the Cy signal when the image of the signal-generation target A in the first region (blue) a is acquired can be subtracted from the Cy signal, so that a part where B is mixed can be removed, whereby a white-light image with high color reproducibility can be generated.

In this case, it is preferable that a B signal in close proximity to an Mg pixel be used when the RGB converter 13 calculates an R signal, and that a B signal in close proximity to a Cy pixel be used when the RGB converter 13 calculates a G signal. If there is a change of color in the observation site, a smooth color change can be reproduced by using information obtained by acquiring an image of a position in close proximity.

Figure 12:
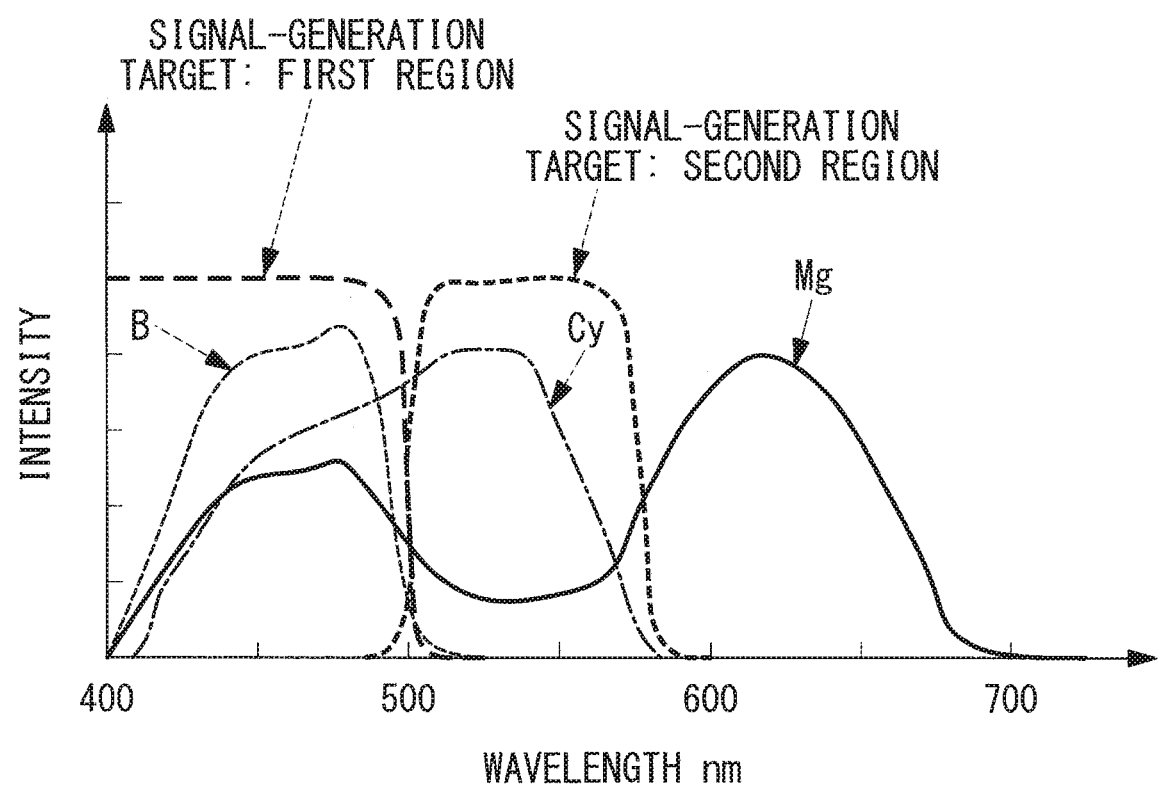
FIG. 12 illustrates a modification of the spectral characteristics of the color filters in FIG. 10.

As shown in FIG. 12, if the spectral characteristic of the Mg color filter has high intensity in the G region, it is preferable that the following configuration be employed.

Specifically, the ratio calculator 12 may calculate the ratio between the B signal and the Mg signal and the ratio between the Cy signal and the Mg signal, and the RGB converter 13 may generate an R signal and a G signal based on the two ratios.

In this case, the B signal and the Mg signal to be used for calculating the ratio are signals acquired when an image of the signal-generation target A shown in FIG. 6 or 7 is acquired.

The calculation in the RGB converter 13 in this case may be performed in accordance with mathematical expression 10.

$$\begin{pmatrix} R \\ G \\ B \end{pmatrix} = \begin{pmatrix} 1 & -gMg/gCy & -bMg/bB \\ 0 & 1 & -bCy/bB \\ 0 & 0 & 1 \end{pmatrix} \begin{pmatrix} Mg \\ Cy \\ B \end{pmatrix} \quad \{\text{Expression 10}\}$$

In this case, gCy denotes a Cy signal when an image of the second region (green) b of the signal-generation target A is acquired.

Accordingly, a signal in the B region corresponding to the ratio between the B signal and the Mg signal when the image of the first region a of the signal-generation target A is acquired can be subtracted from the Mg signal, and a signal in the G region corresponding to the ratio between the Cy signal and the Mg signal when the image of the second region b is acquired can be subtracted from the Mg signal. This is advantageous in that a part where B and G are mixed can be removed, so that a white-light image with high color reproducibility can be generated.

Figure 13:
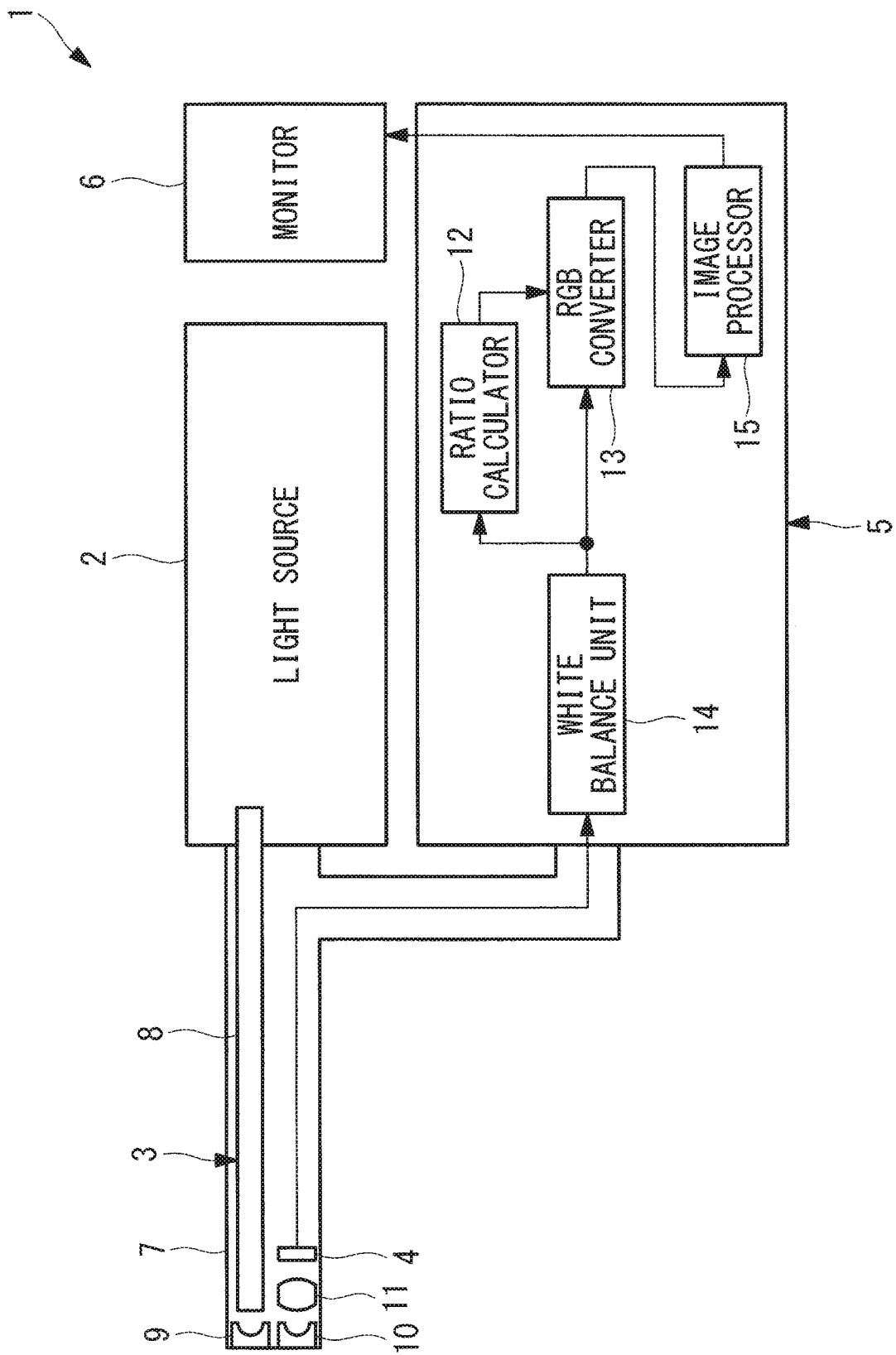
FIG. 13 illustrates the overall configuration of a modification of the endoscope system in FIG. 1.

In each of the above embodiments, the white balance unit 14 adjusts the white balance by using the R signal, the G signal, and the B signal generated in the RGB converter 13. Alternatively, as shown in FIG. 13, the ratio calculation and the RGB conversion may be performed after the white balance unit 14 receives signals acquired by the image pickup device 4 and adjusts the white balance.

In a case of LED illumination in each of the above embodiments, the method that may be used may involve radiating light only in the B region onto a white target, radiating white light onto the white target immediately thereafter, and adjusting the white balance.

As a result, the following aspects are derived from the above embodiments.

An aspect of the present invention provides an endoscope system including an image pickup device having three types of B, G, and Mg color filters and an image processor that generates an image by processing a signal acquired by the image pickup device. The image processor includes a ratio calculator that calculates a ratio between a B signal and an Mg signal, and also includes an R-signal generator that generates an R signal based on the ratio calculated by the ratio calculator.

According to this aspect, since the Mg signal acquired by the image pickup device has an R signal and a B signal mixed therein, the ratio calculator calculates the ratio between the B signal and the Mg signal, and the R-signal generator generates the R signal based on the ratio, so that, by using the R signal and the G signal having no B signal mixed therein and the B signal, a white-light image with high color reproducibility can be generated without color mixing.

In the above aspect, the B signal and the Mg signal used for calculating the ratio in the ratio calculator are preferably signals acquired when an image is acquired under an image acquisition condition in which light having high intensity in a B region in the spectral characteristic and having relatively low intensity in an R region in the spectral characteristic enters the image pickup device.

Accordingly, the image is acquired under the image acquisition condition in which light having high intensity in the B region in the spectral characteristic and having relatively low intensity in the R region in spectral characteristic enters the image pickup device, so that a signal in the B region not affected by the R region can be obtained by an Mg pixel.

In the above aspect, the R-signal generator may generate the R signal based on the following expression.

$$\begin{pmatrix} R \\ G \\ B \end{pmatrix} = \begin{pmatrix} 1 & 0 & -bMg/bB \\ 0 & 1 & 0 \\ 0 & 0 & 1 \end{pmatrix} \begin{pmatrix} Mg \\ G \\ B \end{pmatrix} \quad \{\text{Expression 1}\}$$

In this case, bB denotes the B signal when the image is acquired under the image acquisition condition in which the light having high intensity in the B region in the spectral characteristic enters the image pickup device, and bMg denotes the Mg signal when the image is acquired under the image acquisition condition in which the light having high intensity in the B region in the spectral characteristic enters the image pickup device.

Accordingly, the signal in the B region corresponding to the ratio between the B signal and the Mg signal when the image is acquired under the image acquisition condition in which the light in the B region enters the image pickup device can be subtracted from the Mg signal, so that a part where B is mixed can be removed, whereby a white-light image with high color reproducibility can be generated.

In the above aspect, the B signal when generating the R signal may be a signal of a B pixel in close proximity to an Mg pixel.

Accordingly, even in a case where an image of a target having a change of color is to be acquired, a smooth color change can be reproduced.

Another aspect of the present invention provides an image acquisition method including a first step for performing image acquisition under a first image acquisition condition in which light having high intensity in a B region in the spectral characteristic and having relatively low intensity in an R region in the spectral characteristic enters an image pickup device, and a second step for performing image acquisition substantially simultaneously with the first step under a second image acquisition condition in which light having uniform intensity in R, G, and B regions in the spectral characteristic enters the image pickup device.

According to this aspect, the image acquisition is performed under the first image acquisition condition so that a signal in the B region to be used when generating an R signal can be obtained, whereby the ratio can be calculated with high accuracy. When performing the image acquisition under the first image acquisition condition, the image acquisition under the second image acquisition condition is performed substantially at the same time, so that the white balance can be acquired at the same time, thereby saving time and effort.

Another aspect of the present invention provides an endoscope system including an image pickup device having three types of B, G, and Mg color filters and an image processor that generates an image by processing a signal acquired by the image pickup device. The image processor includes a ratio calculator that calculates a ratio between a B signal and an Mg signal and a ratio between a G signal and the Mg signal, and also includes an R-signal generator that generates an R signal based on the ratios calculated by the ratio calculator.

According to this aspect, the Mg signal acquired by the image pickup device may sometimes have a G signal mixed therein in addition to an R signal and a B signal. The ratio calculator calculates the ratio between the B signal and the Mg signal and the ratio between the G signal and the Mg signal, and the R-signal generator generates the R signal based on these ratios, so that, by using the R signal and the G signal having no B signal mixed therein and the B signal, a white-light image with high color reproducibility can be generated without color mixture.

In the above aspect, the B signal and the Mg signal used by the ratio calculator for calculating the ratio may be signals acquired when an image is acquired under an image acquisition condition in which light having high intensity in a B region in the spectral characteristic and having relatively low intensity in a G region and an R region in the spectral characteristic enters the image pickup device, and the G signal and the Mg signal used by the ratio calculator for calculating the ratio may be signals acquired when an image is acquired under an image acquisition condition in which light having high intensity in the G region in the spectral characteristic and having relatively low intensity in the B region and the R region in the spectral characteristic enters the image pickup device.

Accordingly, the image is acquired under the image acquisition condition in which the light having high intensity in the B region in the spectral characteristic and having relatively low intensity in the G region and the R region in the spectral characteristic enters the image pickup device, so that a signal in the B region not affected by the G region and the R region can be obtained by an Mg pixel. Likewise, the image is acquired under the image acquisition condition in which the light having high intensity in the G region in the spectral characteristic and having relatively low intensity in the B region and the R region in the spectral characteristic enters the image pickup device, so that a signal in the G region not affected by the B region and the R region can be obtained by an Mg pixel.

In the above aspect, the R-signal generator may generate the R signal based on the following expression.

$$\begin{pmatrix} R \\ G \\ B \end{pmatrix} = \begin{pmatrix} 1 & -gMg/gG & -bMg/bB \\ 0 & 1 & 0 \\ 0 & 0 & 1 \end{pmatrix} \begin{pmatrix} Mg \\ G \\ B \end{pmatrix} \quad \{\text{Expression 2}\}$$

In this case, bB denotes the B signal when the image is acquired under the image acquisition condition in which the light having high intensity in the B region in the spectral characteristic enters the image pickup device, bMg denotes the Mg signal when the image is acquired under the image acquisition condition in which the light having high intensity in the B region in the spectral characteristic enters the image pickup device, gG denotes the G signal when the image is acquired under the image acquisition condition in which the light having high intensity in the G region in the spectral characteristic enters the image pickup device, and gMg denotes the Mg signal when the image is acquired under the image acquisition condition in which the light having high intensity in the G region in the spectral characteristic enters the image pickup device.

Accordingly, the signal in the B region corresponding to the ratio between the B signal and the Mg signal when the image is acquired under the image acquisition condition in which the light in the B region enters the image pickup device can be subtracted from the Mg signal, and the signal in the G region corresponding to the ratio between the G signal and the Mg signal when the image is acquired under the image acquisition condition in which the light in the G region enters the image pickup device can be subtracted from the Mg signal, so that a part where B and G is mixed can be removed, whereby a white-light image with high color reproducibility can be generated.

In the above aspect, the B signal and the G signal used when generating the R signal may be signals of a B pixel and a G pixel in close proximity to an Mg pixel.

Accordingly, even in a case where an image of a target having a change of color is to be acquired, a smooth color change can be reproduced.

Another aspect of the present invention provides an image acquisition method including a first step for performing image acquisition under a first image acquisition condition in which light having high intensity in a B region in the spectral characteristic and having relatively low intensity in a G region and an R region in the spectral characteristic enters an image pickup device, and a second step for performing image acquisition under a second image acquisition condition in which light having high intensity in the G region in the spectral characteristic and having relatively low intensity in the B region and the R region in the spectral characteristic enters the image pickup device.

According to this aspect, the image acquisition is performed under the first image acquisition condition so that a signal in the B region can be obtained, and the image acquisition is performed under the second image acquisition condition so that a signal in the G region can be obtained, whereby the ratios can each be calculated with high accuracy.

In the above aspect, the image acquisition method may further include a third step for performing image acquisition under a third image acquisition condition in which light having uniform intensity in the R, G, and B regions in the spectral characteristic enters the image pickup device.

Accordingly, when performing the image acquisition under the first and second image acquisition conditions, the image acquisition under the third image acquisition condition is performed substantially at the same time, so that the white balance can be acquired at the same time, thereby saving time and effort.

Another aspect of the present invention provides an endoscope system including an image pickup device having three types of B, Cy, and R color filters and an image processor that generates an image by processing a signal acquired by the image pickup device. The image processor includes a ratio calculator that calculates a ratio between a B signal and a Cy signal, and also includes a G-signal generator that generates a G signal based on the ratio calculated by the ratio calculator.

According to this aspect, since the Cy signal acquired by the image pickup device has a G signal and a B signal mixed therein, the ratio calculator calculates the ratio between the B signal and the Cy signal, and the G-signal generator generates the G signal based on the ratio, so that, by using the B signal and the G signal and R signal having no B signal mixed therein, a white-light image with high color reproducibility can be generated without color mixing.

In the above aspect, the B signal and the Cy signal used for calculating the ratio in the ratio calculator are preferably signals acquired when an image is acquired under an image acquisition condition in which light having high intensity in a B region in the spectral characteristic and having relatively low intensity in a G region in the spectral characteristic enters the image pickup device.

Accordingly, the image is acquired under the image acquisition condition in which the light having high intensity in the B region in the spectral characteristic and having relatively low intensity in the G region in the spectral characteristic enters the image pickup device, so that a signal in the B region not affected by the G region can be obtained by a Cy pixel.

In the above aspect, the G-signal generator may generate the G signal based on the following expression.

$$\begin{pmatrix} R \\ G \\ B \end{pmatrix} = \begin{pmatrix} 1 & 0 & 0 \\ 0 & 1 & -bCy/bB \\ 0 & 0 & 1 \end{pmatrix} \begin{pmatrix} R \\ Cy \\ B \end{pmatrix} \quad \{\text{Expression 3}\}$$

In this case, bB denotes the B signal when the image is acquired under the image acquisition condition in which the light having high intensity in the B region in the spectral characteristic enters the image pickup device, and bCy denotes the Cy signal when the image is acquired under the image acquisition condition in which the light having high intensity in the B region in the spectral characteristic enters the image pickup device.

Accordingly, the signal in the B region corresponding to the ratio between the B signal and the Cy signal when the image is acquired under the image acquisition condition in which the light in the B region enters the image pickup device can be subtracted from the Cy signal, so that a part where B is mixed can be removed, whereby a white-light image with high color reproducibility can be generated.

In the above aspect, the B signal when generating the G signal may be a signal of a B pixel in close proximity to a Cy pixel.

Accordingly, even in a case where an image of a target having a change of color is to be acquired, a smooth color change can be reproduced.

Another aspect of the present invention provides an image acquisition method including a first step for performing image acquisition under a first image acquisition condition in which light having high intensity in a B region in the spectral characteristic and having relatively low intensity in a G region in the spectral characteristic enters an image pickup device, and a second step for performing image acquisition substantially simultaneously with the first step under a second image acquisition condition in which light having uniform intensity in R, G, and B regions in the spectral characteristic enters the image pickup device imaging element.

According to this aspect, the image acquisition is performed under the first image acquisition condition so that a signal in the B region to be used when generating a G signal can be obtained, whereby the ratio can be calculated with high accuracy. When performing the image acquisition under the first image acquisition condition, the image acquisition under the second image acquisition condition is performed substantially at the same time, so that the white balance can be acquired at the same time, thereby saving time and effort.

Another aspect of the present invention provides an endoscope system including an image pickup device having three types of B, Cy, and Mg color filters and an image processor that generates an image by processing a signal acquired by the image pickup device. The image processor includes a ratio calculator that calculates a ratio between a B signal and an Mg signal and a ratio between the B signal and a Cy signal, and also includes an RG-signal generator that generates an R signal and a G signal based on the ratios calculated by the ratio calculator.

According to this aspect, since the Cy signal acquired by the image pickup device has a G signal and a B signal mixed therein, and the Mg signal has an R signal and a B signal mixed therein, the ratio calculator calculates the ratio between the B signal and the Mg signal and the ratio between the B signal and the Cy signal, and the RG-signal generator generates the R signal and the G signal based on these ratios, so that, by using the B signal and the G signal and R signal having no B signal mixed therein, a white-light image with high color reproducibility can be generated without color mixing.

In the above aspect, the B signal, the Mg signal, and the Cy signal used for calculating the ratios in the ratio calculator are preferably signals acquired when an image is acquired under an image acquisition condition in which light having high intensity in a B region in the spectral characteristic and having relatively low intensity in a G region and an R region in the spectral characteristic enters the image pickup device.

Accordingly, the image is acquired under the image acquisition condition in which the light having high intensity in the B region in the spectral characteristic and having relatively low intensity in the G region and the R region in the spectral characteristic enters the image pickup device, so that a signal in the B region not affected by the R region and the G region can be obtained by an Mg pixel and a signal in the B region not affected by the R region and the G region can be obtained by a Cy pixel.

In the above aspect, the RG-signal generator may generate the R signal and the G signal based on the following expression.

$$\begin{pmatrix} R \\ G \\ B \end{pmatrix} = \begin{pmatrix} 1 & 0 & -bMg/bB \\ 0 & 1 & -bCy/bB \\ 0 & 0 & 1 \end{pmatrix} \begin{pmatrix} Mg \\ Cy \\ B \end{pmatrix} \quad \{\text{Expression 4}\}$$

In this case, bB denotes the B signal when the image is acquired under the image acquisition condition in which the light having high intensity in the B region in the spectral characteristic enters the image pickup device, bMg denotes the Mg signal when the image is acquired under the image acquisition condition in which the light having high intensity in the B region in the spectral characteristic enters the image pickup device, and bCy denotes the Cy signal when the image is acquired under the image acquisition condition in which the light having high intensity in the B region in the spectral characteristic enters the image pickup device.

Accordingly, the signal in the B region corresponding to the ratio between the B signal and the Mg signal when the image is acquired under the image acquisition condition in which the light having high intensity in the B region in the spectral characteristic enters the image pickup device can be subtracted from the Mg signal, so that a part where B is mixed can be removed, whereby a white-light image with high color reproducibility can be generated.

The signal in the B region corresponding to the ratio between the B signal and the Cy signal when the image is acquired under the image acquisition condition in which the light having high intensity in the B region in the spectral characteristic enters the image pickup device can be subtracted from the Cy signal, so that a part where B is mixed can be removed, whereby a white-light image with high color reproducibility can be generated.

In the above aspect, the B signal when generating the R signal may be a signal of a B pixel in close proximity to an Mg pixel, and the B signal when generating the G signal may be a signal of a B pixel in close proximity to a Cy pixel.

Accordingly, even in a case where an image of a target having a change of color is to be acquired, a smooth color change can be reproduced.

Another aspect of the present invention provides an image acquisition method including a first step for performing image acquisition under a first image acquisition condition in which light having high intensity in a B region in the spectral characteristic and having relatively low intensity in a G region and an R region in the spectral characteristic enters an image pickup device, and a second step for performing image acquisition substantially simultaneously with the first step under a second image acquisition condition in which light having uniform intensity in R, G, and B regions in the spectral characteristic enters the image pickup device.

According to this aspect, by performing the image acquisition under the first image acquisition condition, it is possible to generate a B signal, an Mg signal, and a Cy signal in the B region to be used when generating an R signal and a G signal, and thus the ratio can be calculated with high accuracy. When performing the image acquisition under the first image acquisition condition, the image acquisition under the second image acquisition condition is performed substantially at the same time, so that the white balance can be acquired at the same time, thereby saving time and effort.

Another aspect of the present invention provides an endoscope system including an image pickup device having three types of B, Cy, and Mg color filters and an image processor that generates an image by processing a signal acquired by the image pickup device. The image processor includes a ratio calculator that calculates a ratio between a B signal and an Mg signal, a ratio between the B signal and a Cy signal, and a ratio between the Cy signal and the Mg signal, and also includes an RG-signal generator that generates an R signal and a G signal based on the ratios calculated by the ratio calculator.

According to this aspect, since the Cy signal acquired by the image pickup device has a G signal and a B signal mixed therein, and the Mg signal has a G signal in addition to an R signal and a B signal mixed therein, the ratio calculator calculates the ratio between the B signal and the Mg signal and the ratio between the Mg signal and the Cy signal, and the RG-signal generator generates the R signal based on these ratios. Moreover, the ratio calculator calculates the ratio between the B signal and the Cy signal, and the RG-signal generator generates the G signal based on this ratio.

Consequently, by using the B signal and the R signal and G signal having no B signal mixed therein, a white-light image with high color reproducibility can be generated without color mixing.

In the above aspect, the B signal and the Mg signal used by the ratio calculator for calculating the ratio between the B signal and the Mg signal and the ratio between the B signal and the Cy signal may be signals acquired when an image is acquired under an image acquisition condition in which light having high intensity in a B region in the spectral characteristic and having relatively low intensity in a G region and an R region in the spectral characteristic enters the image pickup device, and the Cy signal and the Mg signal used by the ratio calculator for calculating the ratio between the Cy signal and the Mg signal may be signals acquired when an image is acquired under an image acquisition condition in which light having high intensity in the G region in the spectral characteristic and having relatively low intensity in the B region and the R region in the spectral characteristic enters the image pickup device.

Accordingly, the image is acquired under the image acquisition condition in which the light having high intensity in the B region in the spectral characteristic and having relatively low intensity in the G region and the R region in the spectral characteristic enters the image pickup device, so that a signal in the B region not affected by the R region and the G region can be obtained by an Mg pixel and a signal in the B region not affected by the R region and the G region can be obtained by a Cy pixel.

Likewise, the image is acquired under the image acquisition condition in which the light having high intensity in the G region in the spectral characteristic and having relatively low intensity in the B region and the R region in the spectral characteristic enters the image pickup device, so that a signal in the G region not affected by the B region and the R region can be obtained by an Mg pixel.

In the above aspect, the RG-signal generator may generate the R signal and the G signal based on the following expression.

$$\begin{pmatrix} R \\ G \\ B \end{pmatrix} = \begin{pmatrix} 1 & -gMg/gCy & -bMg/bB \\ 0 & 1 & -bCy/bB \\ 0 & 0 & 1 \end{pmatrix} \begin{pmatrix} Mg \\ Cy \\ B \end{pmatrix} \quad \{\text{Expression 5}\}$$

In this case, bB denotes the B signal when the image is acquired under the image acquisition condition in which the light having high intensity in the B region in the spectral characteristic enters the image pickup device, bMg denotes the Mg signal when the image is acquired under the image acquisition condition in which the light having high intensity in the B region in the spectral characteristic enters the image pickup device, bCy denotes the Cy signal when the image is acquired under the image acquisition condition in which the light having high intensity in the B region in the spectral characteristic enters the image pickup device, gMg denotes the Mg signal when the image is acquired under the image acquisition condition in which the light having high intensity in the G region in the spectral characteristic enters the image pickup device, and gCy denotes the Cy signal when the image is acquired under the image acquisition condition in which the light having high intensity in the G region in the spectral characteristic enters the image pickup device.

Accordingly, the signal in the B region corresponding to the ratio between the B signal and the Mg signal when the image is acquired under the image acquisition condition in which the light in the B region enters the image pickup device can be subtracted from the Mg signal, so that a part where B is mixed can be removed. The signal in the G region corresponding to the ratio between the Cy signal and the Mg signal when the image is acquired under the image acquisition condition in which the light in the G region enters the image pickup device can be subtracted from the Mg signal, so that a part where G is mixed can be removed. The signal in the B region corresponding to the ratio between the B signal and the Cy signal when the image is acquired under the image acquisition condition in which the light in the B region enters the image pickup device can be subtracted from the Cy signal, so that a part where B is mixed can be removed. Consequently, a white-light image with high color reproducibility can be generated.

In the above aspect, the B signal and the Cy signal used when generating the R signal may be signals of a B pixel and a Cy pixel in close proximity to an Mg pixel, and the B signal used when generating the G signal may be a signal of a B pixel in close proximity to a Cy pixel.

Accordingly, even in a case where an image of a target having a change of color is to be acquired, a smooth color change can be reproduced.

REFERENCE SIGNS LIST 1 endoscope system
4 image pickup device
5 image processor
12 ratio calculator
13 RGB converter (R-signal generator, G-signal generator, RG-signal generator)

The invention claimed is:
1. An endoscope system comprising:
an image pickup device having three types of color filters, said types being blue, green, and magenta; and
an image processor that generates an image by processing a signal acquired by the image pickup device,
wherein the image processor includes a ratio calculator that calculates a ratio of a magenta signal to a blue signal by using the blue signal and the magenta signal acquired when an image of a blue target is acquired by using white light and that calculates a ratio of a magenta signal to a green signal by using the green signal and the magenta signal acquired when an image of a green target is acquired by using white light, and also includes a red-signal generator that generates a red signal based on the ratio of the magenta signal to the blue signal and the ratio of the magenta signal to the green signal calculated by the ratio calculator.

2. The endoscope system according to claim 1, wherein the red-signal generator generates the red signal based on an expression indicated below:

$$\begin{pmatrix} R \\ G \\ B \end{pmatrix} = \begin{pmatrix} 1 & -gMg/gG & -bMg/bB \\ 0 & 1 & 0 \\ 0 & 0 & 1 \end{pmatrix} \begin{pmatrix} Mg \\ G \\ B \end{pmatrix}$$

where bB denotes the blue signal acquired when the image of the blue target is acquired by using the white light, bMg denotes the magenta signal acquired when the image of the blue target is acquired by using the white light, gG denotes the green signal acquired when the image of the green target is acquired by using the white light, and gMg denotes the magenta signal acquired when the image of the green target is acquired by using the white light.

3. The endoscope system according to claim 1, wherein the blue signal and the green signal when generating the red signal are signals of a blue pixel and a green pixel in close proximity to a magenta pixel.

4. An endoscope system comprising:
an image pickup device having three types of color filters, said types being blue, cyan, and magenta; and
an image processor that generates an image by processing a signal acquired by the image pickup device,
wherein the image processor includes a ratio calculator that calculates a ratio of a magenta signal to a blue signal and a ratio of a cyan signal to the blue signal by using the blue signal, the magenta signal, and the cyan signal acquired when an image of a blue target is acquired by using white light and that calculates a ratio of a magenta signal to a cyan signal by using the cyan signal and the magenta signal acquired when an image of a green target is acquired by using white light, and also includes a red-green-signal generator that generates a red signal based on the ratio of the magenta signal to the blue signal and the ratio of the magenta signal to the cyan signal calculated by the ratio calculator and that generates a green signal based on the ratio of the cyan signal to the blue signal calculated by the ratio calculator.

5. The endoscope system according to claim 4, wherein the red-green-signal generator generates the red signal and the green signal based on an expression indicated below:

$$\begin{pmatrix} R \\ G \\ B \end{pmatrix} = \begin{pmatrix} 1 & -gMg/gCy & -bMg/bB \\ 0 & 1 & -bCy/bB \\ 0 & 0 & 1 \end{pmatrix} \begin{pmatrix} Mg \\ Cy \\ B \end{pmatrix}$$

where bB denotes the blue signal acquired when the image of the blue target is acquired by using the white light, bMg denotes the magenta signal acquired when the image of the blue target is acquired by using the white light, bCy denotes the cyan signal acquired when the image of the blue target is acquired by using the white light, gMg denotes the magenta signal acquired when the image of the green target is acquired by using the white light, and gCy denotes the cyan signal acquired when the image of the green target is acquired by using the white light.

6. The endoscope system according to claim 4, wherein the blue signal and the cyan signal when generating the red signal are signals of a blue pixel and a cyan pixel in close proximity to a magenta pixel, and
wherein the blue signal when generating the green signal is a signal of a blue pixel in close proximity to a cyan pixel.

7. An endoscope system comprising:
an image pickup device having three types of color filters, said types being blue, green, and magenta; and
an image processor that generates an image by processing a signal acquired by the image pickup device,
wherein the image processor includes a ratio calculator that calculates a ratio of a magenta signal to a blue signal by using the blue signal and the magenta signal acquired when an image of a white target is acquired by using blue light and that calculates a ratio of a magenta signal to a green signal by using the green signal and the magenta signal acquired when an image of the white target is acquired by using green light, and also includes a red-signal generator that generates a red signal based on the ratio of the magenta signal to the blue signal and the ratio of the magenta signal to the green signal calculated by the ratio calculator.

8. An endoscope system comprising:

an image pickup device having three types of color filters, said types being blue, cyan, and magenta; and an image processor that generates an image by processing a signal acquired by the image pickup device, wherein the image processor includes a ratio calculator that calculates a ratio of a magenta signal to a blue signal and a ratio of a cyan signal to the blue signal by using the blue signal, the magenta signal, and the cyan signal acquired when an image of a white target is acquired by using blue light and that calculates a ratio of a magenta signal to a cyan signal by using the cyan signal and the magenta signal acquired when an image of the white target is acquired by using green light, and also includes a red-green-signal generator that generates a red signal based on the ratio of the magenta signal to the blue signal and the ratio of the magenta signal to the cyan signal calculated by the ratio calculator and that generates a green signal based on the ratio of the cyan signal to the blue signal calculated by the ratio calculator.

* * * * *